United States Patent [19]
Sensui

[11] Patent Number: 5,541,701
[45] Date of Patent: Jul. 30, 1996

[54] EYE DIRECTION DETECTING APPARATUS OF CAMERA VIEW FINDER

[75] Inventor: Takayuki Sensui, Tokyo, Japan

[73] Assignee: Asahi Kogaku Kogyo Kabushiki Kaisha, Tokyo, Japan

[21] Appl. No.: 224,181

[22] Filed: Apr. 7, 1994

Related U.S. Application Data

[63] Continuation of Ser. No. 999,375, Dec. 31, 1992, abandoned.

[30]     Foreign Application Priority Data

Jan. 13, 1992  [JP]  Japan ................................ 4-042469
Jan. 13, 1992  [JP]  Japan ................................ 4-042470

[51] Int. Cl.$^6$ ..................................................... G03B 7/00
[52] U.S. Cl. ............................. 354/410; 354/62; 354/219
[58] Field of Search ................................... 354/400, 402, 354/410, 62, 219

[56]             References Cited

U.S. PATENT DOCUMENTS

Re. 31,370   9/1983   Mashimo et al. .
3,701,309   10/1972   Thiele et al. .
4,047,187    9/1977   Mashimo et al. .
4,183,642    1/1980   Fukuoka .
4,287,410    9/1983   Crane et al. .
4,445,757    5/1984   Enomoto et al. .
4,508,443    4/1985   Matsuzaki et al. .
4,560,863   12/1985   Matsumura et al. .
4,574,314    3/1986   Weinblatt .
4,636,624    1/1987   Ishida et al. .
4,786,934   11/1988   Kunze et al. .
4,828,381    5/1989   Shindo .

(List continued on next page.)

FOREIGN PATENT DOCUMENTS 55338    7/1982   European Pat. Off. .
2382056    9/1978   France .
1211815    3/1966   Germany .
3331264    3/1984   Germany .
3336265    4/1984   Germany .
3505864    8/1985   Germany .
3841575    7/1989   Germany .
59-102202   6/1984   Japan .
61-172552   8/1986   Japan .
62-22561    2/1987   Japan .
1277533    11/1988  Japan .
1-241511    9/1989   Japan .
1412707    11/1975  United Kingdom .
 871571    3/1987   WIPO .

OTHER PUBLICATIONS

French Search Report and Annex.
United Kingdom Search Report.
An Excerpt from the book "Techische Optik" by G. Schroder, (Vogel–Verlag) p. 41, section 2.3.4. with an English language translation of the section.
"Methods and Design–Survey of Eye Movement Recording Methods" by Young and Shenna, Behavior Research–Methods and Instrumentation, pp. 397–429 (vol. 7 (5), 1975).
"Psychological Physic of Vision", by Mitsuo Ikeda, 1975.
"Fixation Point Measurement by the Oculometer Technique" by John Merchant, Optical Engineering Jul. 8, 1974.

Primary Examiner—Russell E. Adams
Attorney, Agent, or Firm—Sandler, Greenblum & Bernstein

[57]             ABSTRACT

An eye direction detecting apparatus of a camera having a view finder in which a bundle of rays reflected from an object to be photographed and transmitted through a taking lens is made incident on a photographer's eye to form an erect image thereof by an image erecting optical element. The apparatus includes a light emitting optical system which emits measuring light to be made incident upon the photographer's eye through a part of the view finder, and a light receiving optical system which receives light reflected from the photographer's eye to detect the eye direction. The light emitting optical system and the light receiving optical system are arranged so that optical axes thereof lie in a plane normal to an optical axis of a bundle of rays incident upon the image erecting optical element through the taking lens.

24 Claims, 10 Drawing Sheets

U.S. PATENT DOCUMENTS

| | | | |
|---|---|---|---|
| 5,036,347 | 7/1991 | Tsunekawa et al. | 354/400 |
| 5,155,516 | 10/1992 | Shindo . | |
| 5,182,443 | 1/1993 | Suda et al. | 354/400 |
| 5,214,466 | 5/1993 | Nagano et al. | 354/402 |
| 5,225,862 | 7/1993 | Nagano et al. | 354/400 |
| 5,260,734 | 11/1993 | Shindo . | |
| 5,262,807 | 11/1993 | Shindo . | |
| 5,291,234 | 3/1994 | Shindo et al. . | |
| 5,293,535 | 3/1994 | Sensui . | | ns
EYE DIRECTION DETECTING APPARATUS OF CAMERA VIEW FINDER

This application is a continuation of application Ser. No. 07/999,375, filed Dec. 31, 1992, now abandoned.

BACKGROUND OF THE INVENTION

1. Field of the Invention

The present invention relates is directed to an eye direction detecting apparatus that is provided in a single lens reflex camera, and a view finder of a single lens reflex camera having a diopter adjusting device.

2. Description of Related Art

A known eye direction detecting apparatus (referred to as an eye detector) is disclosed, for example, in U.S. Pat. No. 5,036,347. The known eye detector in a single lens reflex camera is provided in the vicinity of a pentagonal prism, so that a bundle of rays emitted from a light source, such as a light emitting diode (LED), is made incident upon a photographer's eye through an eyepiece of the view finder. Light reflected by the photographer's eye is then converged and received by a light receiving element, such as a CCD sensor, whose output is electrically processed to detect the eye direction. In single lens reflex cameras that employ an eye direction detecting apparatus as described above, a significant amount of space is required for the eye direction detecting apparatus, resulting in an excessively large camera.

A view finder of a single lens reflex camera having a diopter adjusting device, in addition to an eye direction detector, is also known. In a known view finder, for example, when the eyepiece closest to a photographer's eye is moved in the optical axis direction to adjust the diopter, the incident angle of the bundle of eye direction detecting rays incident upon the photographer's eye will vary. Consequently, an optical positional relationship between the eye and the light receiving element of the eye detector will vary, resulting in an inaccurate detection of the eye direction.

SUMMARY OF THE INVENTION

The primary object of the present invention is to provide an eye detector in a single lens reflex camera which results in a miniaturization of the camera. In particular, it is an object of the present invention to provide an eye detector which results in the reduction in height of the single lens reflex camera.

Another object of the present invention is to provide a view finder having a diopter adjusting device in which the adjustment of the diopter has no, or minimal influence on the precision of the eye detector.

According to the present invention, a camera having a view finder is provided with an eye direction detecting apparatus, in which a bundle of rays reflected from an object to be photographed and transmitted through a taking lens is made incident on a photographer's eye to form an erect image thereof by an image erecting optical element. The eye direction detecting apparatus includes a light emitting optical system which emits measuring light to be made incident upon the photographer's eye through a part of the view finder, and a light receiving optical system which receives light reflected from the photographer's eye to an eye direction. The light emitting optical system and the light receiving optical system are arranged so that the optical axes thereof lie in a plane normal to an optical axis of a bundle of rays incident upon the image erecting optical element through the taking lens.

Preferably, an eyepiece lens is provided which converges light, reflected from the object to be photographed and transmitted through the taking lens, onto the photographer's eye.

According to another aspect of the present invention, a diopter adjusting device is provided for moving at least a part of the eyepiece lens in the optical axis direction, so that the direction of a bundle of preferably parallel eye direction detecting rays incident upon the photographer's eye does not change upon the adjustment of the diopter.

In a preferred embodiment, a beam splitting mechanism is provided for separating optical paths of the light emitting optical system and the light receiving optical system from the optical path of light reflected from the object to be photographed.

According to still another aspect of the present invention, a view finder is provided in which a bundle of rays reflected from an object to be photographed and transmitted through a taking lens is made incident on a photographer's eye through an eyepiece lens. The view finder includes a light emitting optical system which emits measuring light to be made incident upon the photographer's eye through a part of the view finder, a light receiving optical system which receives light reflected from the photographer's eye to detect eye direction, and a diopter adjusting device for moving at least a part of the eyepiece lens in the optical axis direction, so that the direction of a bundle of rays upon the photographer's eye does not change upon the adjustment of the diopter.

The present disclosure relates to subject matter contained in Japanese patent application Nos. HEI 4-42469 and HEI 4-42470 (both filed on Jan. 13, 1992) which are expressly incorporated herein by reference in their entirety.

BRIEF DESCRIPTION OF THE DRAWINGS

The invention will be described below in detail with reference to the accompanying drawings, in which.

DESCRIPTION OF THE PREFERRED EMBODIMENT

FIGS. 1 through 5 show different embodiments of an eye direction detector that are small in height.

Figure 1:
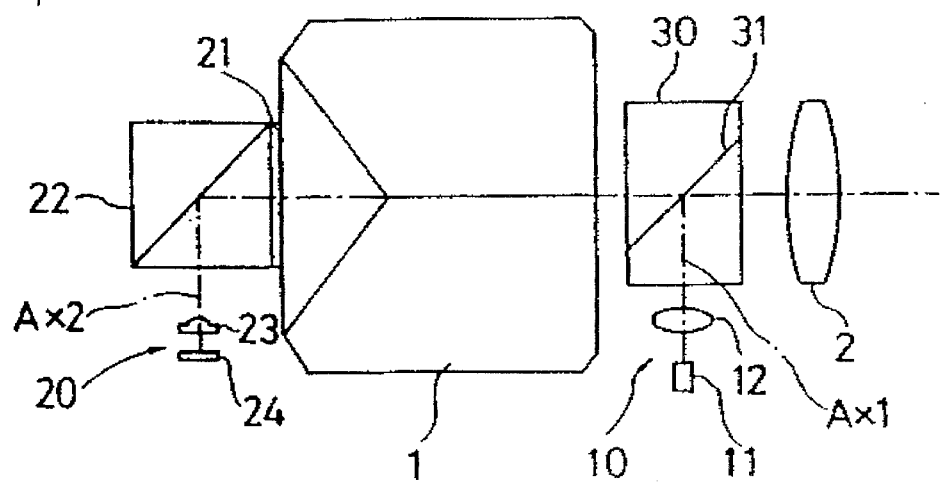
FIG. 1 is a plan view of an eye direction detecting apparatus applied to a single lens reflex camera, according to a first embodiment of the present invention.
Figure 2:
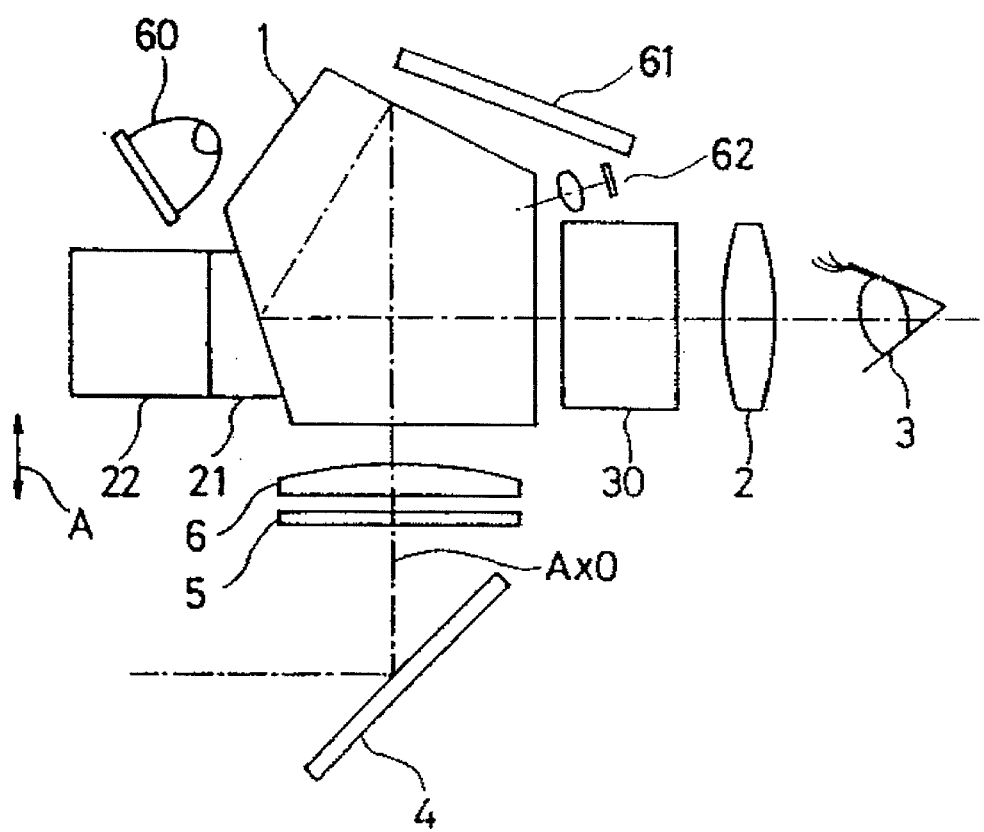
FIG. 2 is a side elevation view of the eye direction detecting apparatus of FIG. 1.

Embodiment 1:

FIGS. 1 and 2 show a first embodiment of an eye direction detecting device (eye detector), incorporated in a view finder of a single lens reflex camera.

In FIGS. 1 and 2, an eye detector includes light emitting, and receiving optical systems 10 and 20, respectively which are provided on opposite sides of a pentagonal prism 1, provided in a view finder of a single lens reflex camera to function as an image erecting optical system.

The light emitting optical system 10 has a light emitting diode 11, as a light source, which emits infrared light.

Divergent light emitted from the light emitting diode 11 is made incident upon a beam splitter 30 through a light projection lens 12. The laser beam incident upon the beam splitter 30 is reflected by a beam splitting surface 31 thereof, collimated by an eyepiece lens 2 of the view finder, and then made incident upon a photographer's eye 3.

The laser beam reflected by the photographer's eye 3 is partly transmitted through the beam splitting surface 31 and is then transmitted through a pentagonal prism 1 and a compensator prism 21 adjacent to the slanted front face of the pentagonal prism 1. The laser beam is then reflected by a total reflection surface of a prism 22 and converged onto a CCD line sensor 24 through an image reforming lens 23. The compensator prism 21 prevents refraction of the light emitted from the prism 1.

The optical elements of the light emitting optical system 10 and the light receiving optical system 20 are arranged so that optical axes Ax1 and Ax2 of the optical systems lie in a plane normal to a center axis Ax0 (FIG. 2) of a bundle of rays incident upon the pentagonal prism 1, i.e., in a plane of the drawing shown in FIG. 1. Consequently, the height of the eye detector in direction A, shown in FIG. 2, can be reduced, providing space above the pentagonal prism large enough to accommodate a retractable strobe 60, a liquid crystal display 61 and/or a light receiving element 62 for the detection of object distance, etc.

The principle of eye direction detection is disclosed in U.S. Pat. No. 5,036,347 mentioned above. Accordingly, no detailed explanation of the apparatus is given herein. In short, an eye direction is detected, for example, in accordance with the positional relationship between a first Purkinje image formed by the light reflected from the eye and a pupil image.

The bundle of rays reflected by a quick-return mirror 4 through a taking lens (not shown), to form an image of an object to be photographed on a focusing screen 5, is converged by a condenser lens 6. The image is formed erect by the pentagonal prism 1, and an additional reflecting surface, such as, for example, the quick-return mirror 4 and is then transmitted through the beam splitter 30 to be made incident upon the photographer's eye 3 through the eyepiece 2.

The surface of the compensator prism 21, that is in contact with the pentagonal prism 1, has a wavelength discrimination property, so that infrared light can be transmitted therethrough, while visible light is reflected thereby. Thus, infrared light of the eye detector is received by the light receiving system 20 and object light is incident upon the photographer's eye.

Figure 3:
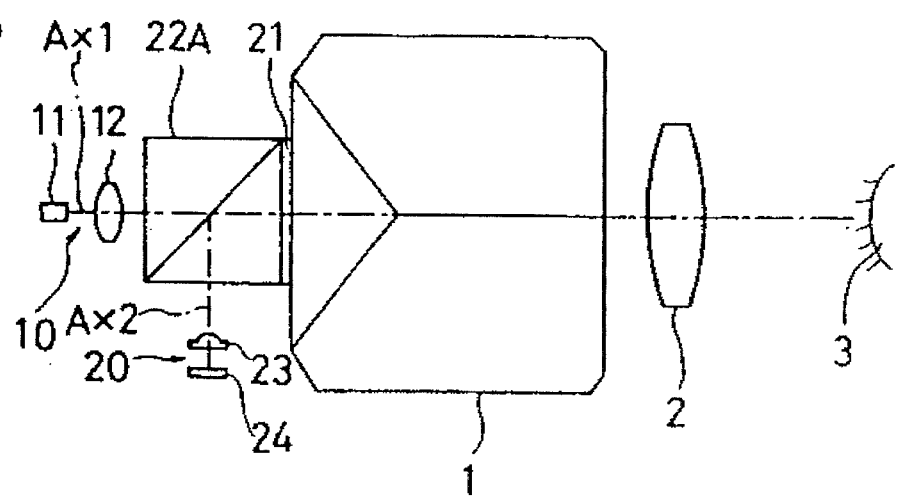
FIG. 3 is a plan view of an eye direction detecting apparatus applied to a single lens reflex camera, according to a second embodiment of the present invention.

Embodiment 2:

FIG. 3 shows a second embodiment of the present invention, in which both the light emitting optical system 10 and the light receiving optical system 20 are located on the same side of the pentagonal prism 1 opposite the photographer's eye 3.

The light emitting optical system 10 includes a light emitting diode 11 and a projection lens 12. The light receiving optical system 20 includes an image reforming lens 23 and a CCD line sensor 24. Measuring light emitted from the light emitting optical system 10 is transmitted through a beam splitter 22A, having a half mirror surface, and is made incident upon the pentagonal prism 1 through the compensator prism 21. Light transmitted through the pentagonal prism 1 is made incident upon the photographer's eye through the eyepiece 2.

Light reflected by the photographer's eye is transmitted through the eye piece 2, the pentagonal prism 1 and the compensator prism 21, and is then reflected by the beam splitter 22A to be converged onto the CCD line sensor 24 through the image reforming lens 23 to form an image.

Figure 4:
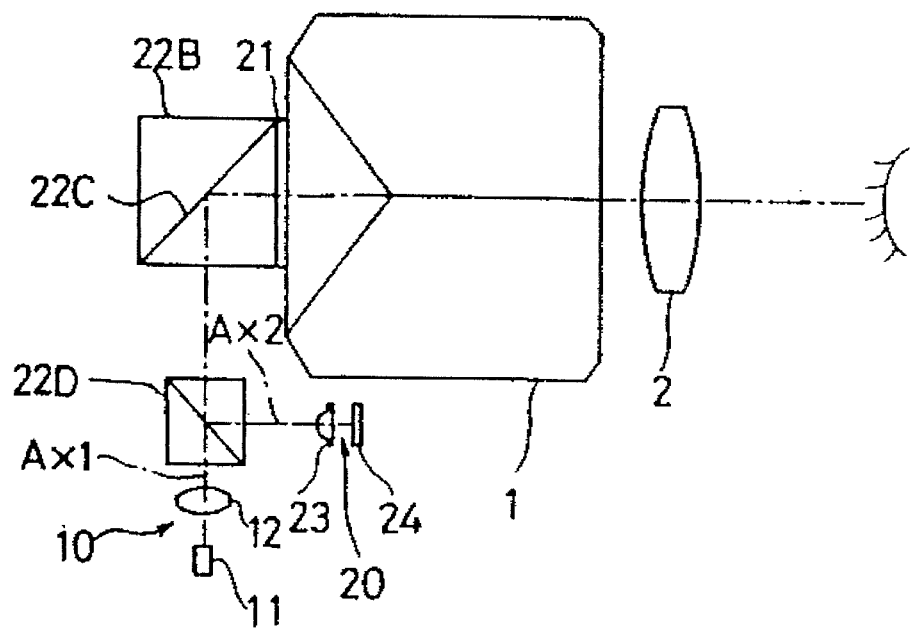
FIG. 4 is a plan view of an eye direction detecting apparatus applied to a single lens reflex camera, according to a third embodiment of the present invention.

In a modified arrangement, shown in FIG. 4, the beam splitter 22A is replaced with a reflector 22B having a total reflection surface 22c. A beam splitter 22D is provided on an optical path of light reflected by the reflector 22B. The light emitting optical system 10 and the light receiving optical system 20 are located on optical paths Ax1 and Ax2, corresponding to transmitted light and reflected light of the beam splitter 22D, respectively.

Figure 5:
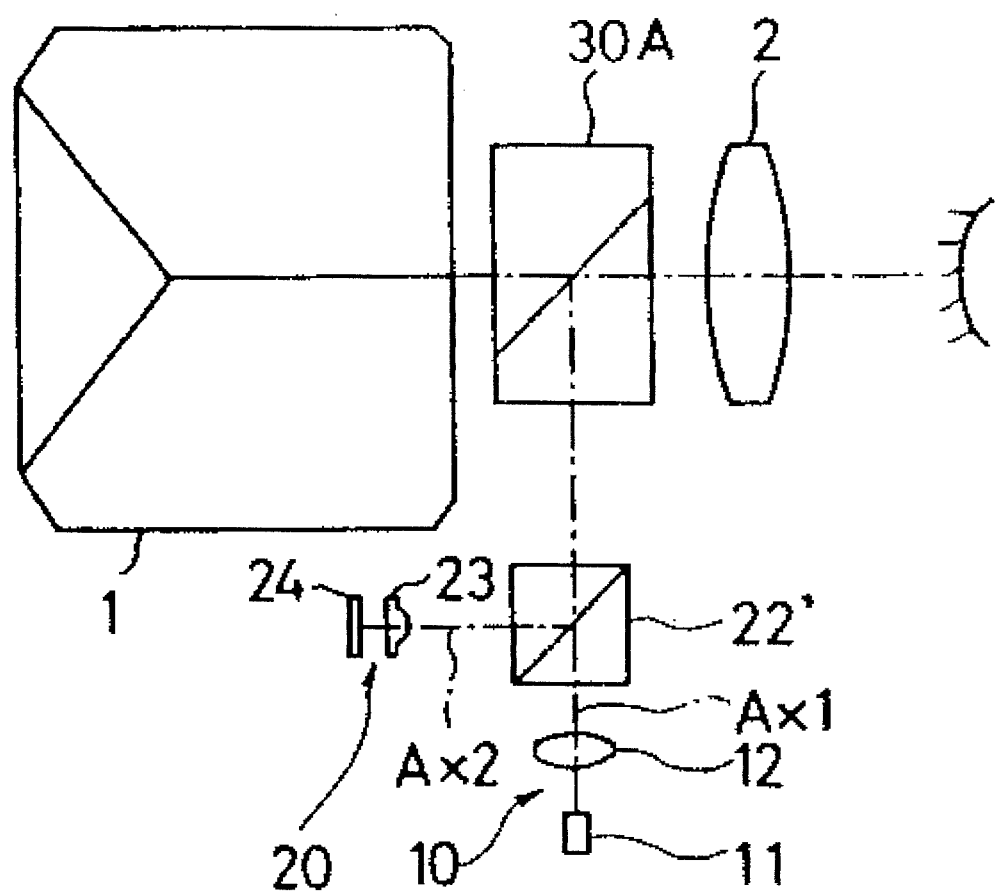
FIG. 5 is a plan view of an eye direction detecting device applied to a single lens reflex camera, according to a fourth embodiment of the present invention.

Embodiment 3:

FIG. 5 shows a third embodiment of the present invention, in which a dichroic prism 30A is provided between the pentagonal prism 1 and the eyepiece 2. The light emitting optical system 10 and the light receiving optical system 20 are located on the same side of the pentagonal prism 1 as the photographer's eye 3.

The dichroic prism 30A reflects the infrared light emitted from the light emitting diode 11, but permits visible light, transmitted through a taking lens (not shown), to pass therethrough. Consequently, a loss of light in the eye detector can be reduced while preserving the light in the field of view of the view finder.

As can be seen from the above discussion, according to the present invention, the space that the eye detector occupies in the height direction of the camera can be reduced by the improved optical element arrangement of the eye detector. Accordingly, a space large enough to accommodate a liquid crystal display panel and/or a retractable strobe, etc., can be provided above the pentagonal prism.

FIGS. 6 through 12 show different embodiments of a single lens reflex camera having a diopter adjusting device in addition to the eye detector, wherein the detection of the eye direction is not influenced by the adjustment of the diopter.

Figure 6:
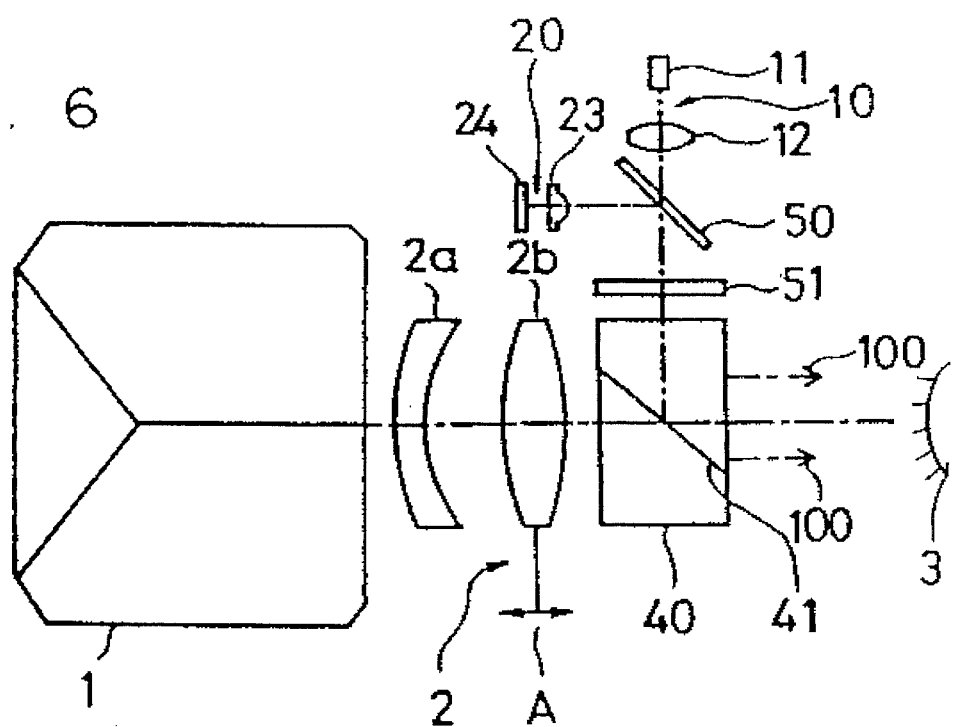
FIGS. 6 through 12 are plan views of a single lens reflex camera having an eye direction detecting device and a diopter adjusting device, according to different embodiments of the present invention.

Embodiment 4:

FIG. 6 shows a fourth embodiment of the present invention, in which a view finder includes an eye detector comprising a pentagonal prism 1, an eyepiece 2 having a negative lens 2a and a positive lens 2b, a dichroic prism 40, and light emitting, and receiving optical systems 10 and 20, respectively provided on an optical path of light separated from the optical axis of the object light by the dichroic prism 40.

The light emitting optical system 10 has a light source (semiconductor laser 11) which emits infrared light. The semiconductor laser 11 is designed so that P-polarized light emitted thereby is made incident upon the a polarization beam splitter 50. Measuring light emitted from the semiconductor laser 11 is transmitted through the polarization beam splitter 50 and converted to circularly polarized light by a ¼ wave plate 51 to be incident upon the dichroic prism 40.

The dichroic prism 40 has a beam splitting surface 41 which reflects infrared light and permits visible light to pass therethrough. Consequently, measuring light emitted from the light emitting optical system is reflected by the beam splitting surface 41 and is made incident upon the photographer's eye 3 as a parallel beam.

The laser beam reflected by the photographer's eye 3 is circularly polarized with a direction of rotation of the field vector opposite that of the incident beam. The circularly polarized beam is reflected again by the splitting surface 41 of the dichroic prism 40 and is then converted to linearly polarized light, which is S-polarized with respect to the polarization beam splitter 50, by the ¼ wave plate 51. Consequently, the reflected laser beam is reflected by the polarization beam splitter 50 and is then converged onto the CCD line sensor 24 through the image reforming lens 23 to form an image.

The positive lens 2b of the eyepiece 2 is movable in an optical axis direction A to adjust the diopter of the view finder in accordance with the eyesight of the photographer. In this arrangement, movement of the positive lens 2b does not affect the positional relationship between the eye detector and the eye 3 (i.e., the optical path of the measuring light is not adversely affected by the movement of the lens 2b), so that the direction of a bundle of eye direction detecting rays 100 upon the photographer's eye does not change upon the adjustment of the diopter. Accordingly, the eye direction can be precisely detected under predetermined conditions, regardless of the adjusted diopter. Preferably, the direction of a bundle of eye direction detecting rays 100 upon the photographer's eye is kept parallel upon the adjustment of the diopter.

Figure 7:
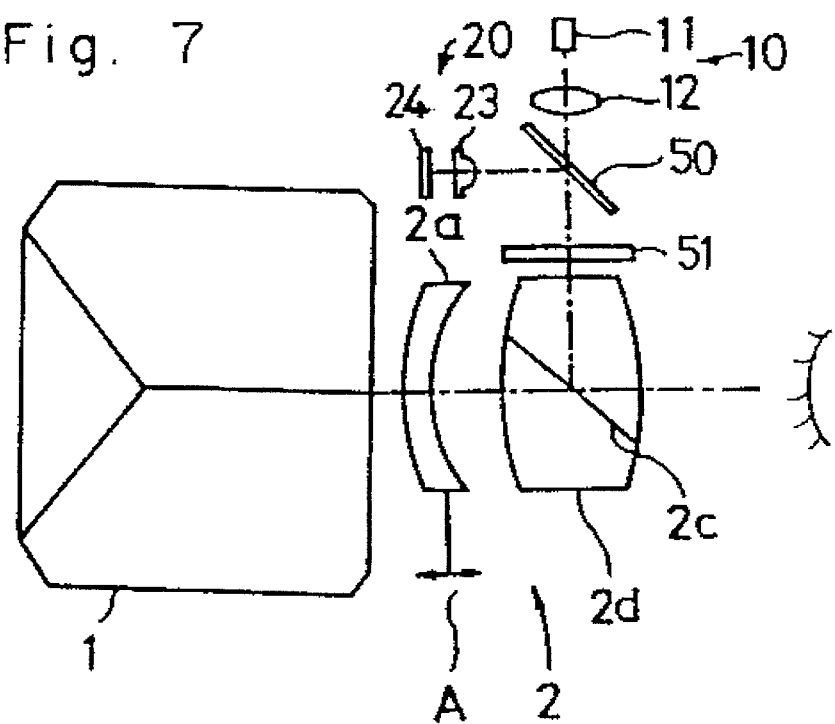
Figure 8:
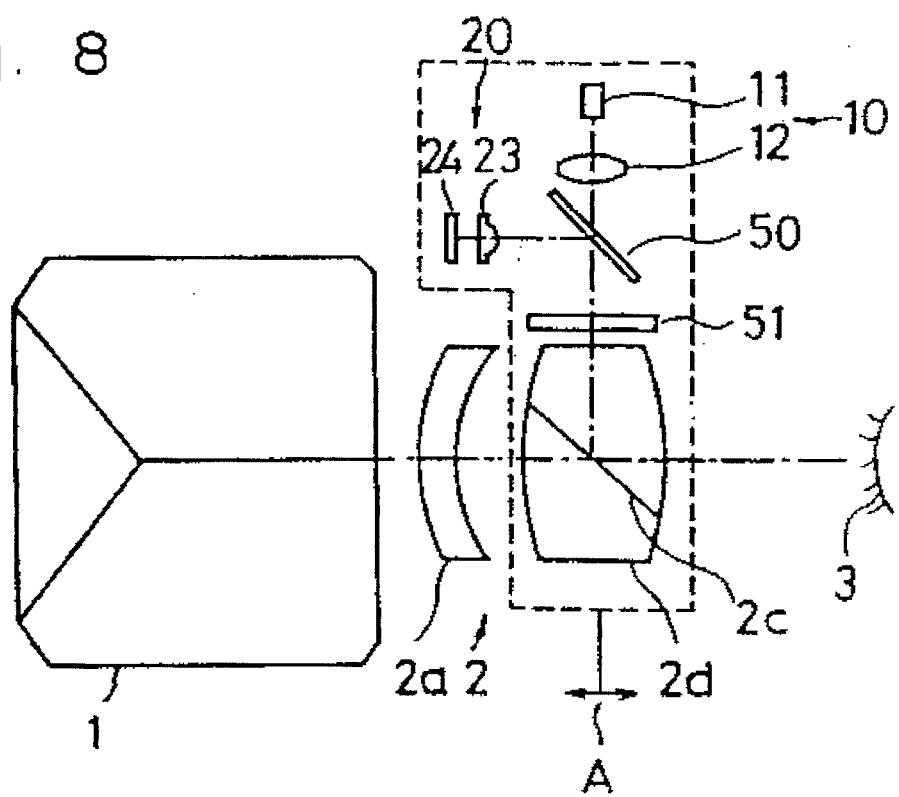

Embodiment 5:

FIGS. 7 and 8 show a fifth embodiment of the present invention, in which the eyepiece 2 comprises a negative lens 2a similar to that shown in FIG. 6 and a positive lens 2d having therein a beam splitting surface (separation surface) 2c which functions as a dichroic mirror. The positive lens 2d has an optical function which is a composite of the positive lens 2b, shown in FIG. 6, and the dichroic prism 40. This reduces the number of optical elements, as compared with the arrangement shown in FIG. 6. Accordingly, less space is required to accommodate the eye detector.

In the arrangement illustrated in FIG. 7, the negative lens 2a is movable in optical axis direction A to control the diopter, similar to the arrangement illustrated in FIG. 6. Again, the adjustment of the diopter has substantially no influence on the eye detector.

In a modified arrangement illustrated in FIG. 8, an assembly, designated by a dotted line, of the positive lens 2d and the light emitting and receiving optical systems 10 and 20, respectively, of the eye detector, is movable in the optical axis direction A of the eyepiece lens 2 to adjust the diopter without adversely affecting the measuring light. Also, in the arrangement illustrated in FIG. 8, there is no change in the optical positional relationship between the eye and the eye direction detector during the adjustment of the diopter. Accordingly, eye direction can be precisely detected by the eye detector under predetermined requirements.

Figure 9:
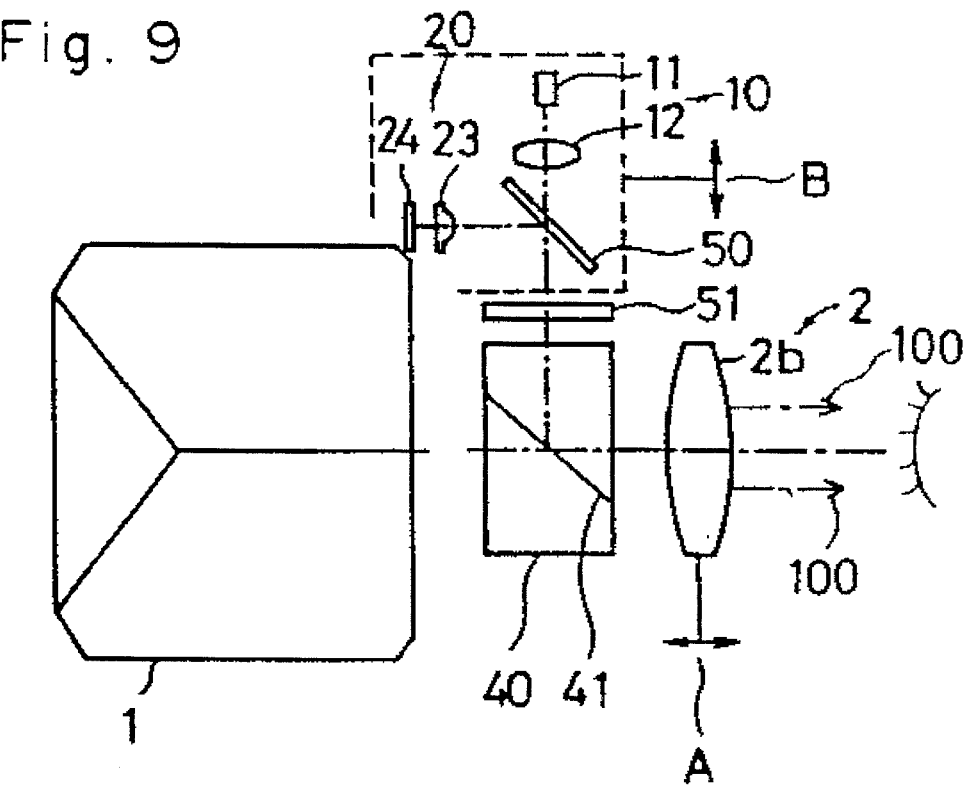
Figure 10:
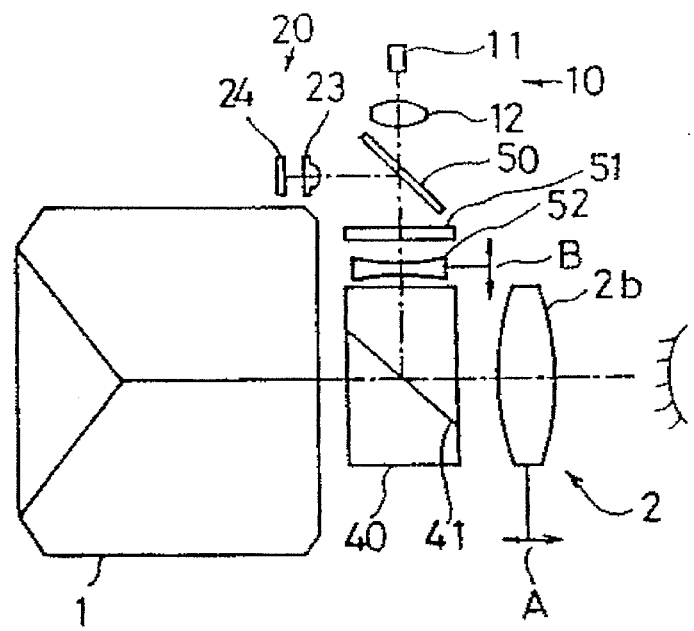

Embodiment 6:

FIGS. 9 and 10 show a sixth embodiment of the present invention, in which the eyepiece lens 2 comprises one positive lens 2b. The dichroic prism 40 is provided between the eyepiece 2 and the pentagonal prism 1.

In the arrangement illustrated in FIG. 9, when the positive lens 2b is moved in the optical axis direction A to control the diopter, the light emitting and receiving optical systems 10 and 20 of the eye detector, designated by the dotted line, are moved with respect to the positive lens 2b in direction B by way of, for example, a cam device. Consequently, a change in the optical path direction of the eye detector, caused by the movement of the positive lens 2b, is cancelled by the movement of the eye detector.

In a modified arrangement illustrated in FIG. 10, a concave lens 52 is provided between the ¼ wave plate 51 and the dichroic prism 40. When the positive lens 2b is moved in optical axis direction A, to control the diopter, the concave lens 52 is moved in direction B to eliminate an adverse affect on the eye detector caused by the adjustment of the diopter. Note that, in the arrangement shown in FIGS. 9 and 10, the movement of the positive lens 2b in direction A and the movement of light emitting and receiving optical system 10 ( the concave lens 52) in direction B are controlled so that the direction of a bundle of eye direction detecting rays 100 upon the photographer's eye does not change upon the adjustment of the diopter, as same as the embodiments shown in FIGS. 6, 7, 8 and 9.

Figure 11:
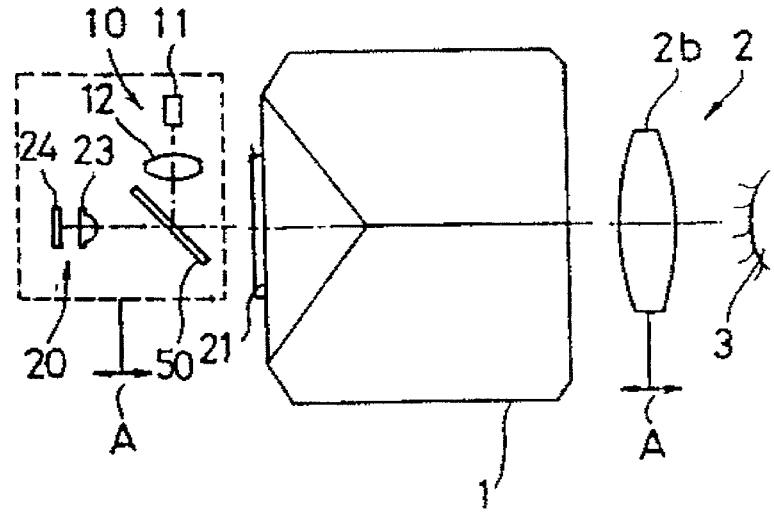
Figure 12:
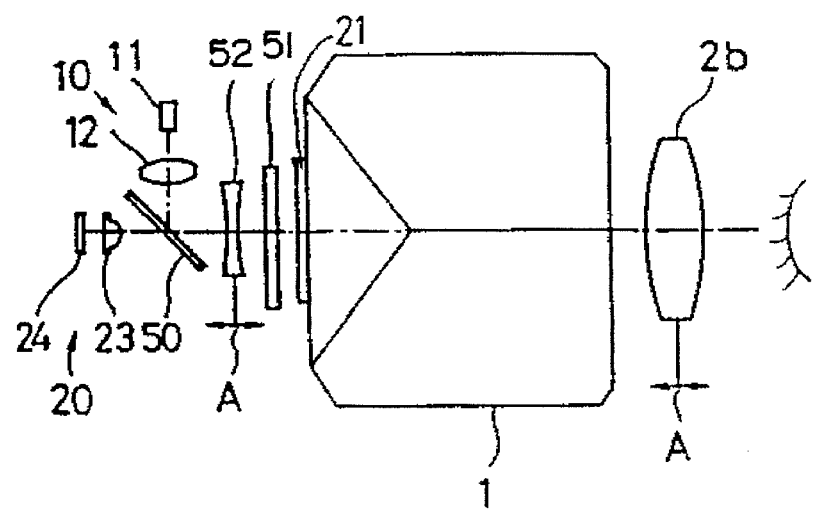

Embodiment 7:

FIGS. 11 and 12 show a seventh embodiment of the present invention, in which the light emitting optical system 10 and the light receiving optical system 20 are provided on the same side of the pentagonal prism 1, opposite the eyepiece lens 2.

The pentagonal prism 1 is provided with a compensator prism 21 on the surface thereof, opposite the eyepiece 2. The connecting surface defines a dichroic surface which reflects visible light and permits infrared light to pass therethrough.

When the eyepiece lens 2 is moved to adjust the diopter, in the arrangement illustrated in FIG. 11, the assembly of the eye detector, designated by a dotted line, is moved as a whole.

In a modified arrangement illustrated in FIG. 12, only a concave lens 52 is moved in an optical axis direction to adjust the diopter. The construction and operation of the other elements of the arrangement shown in FIG. 12 are substantially the same as that of the sixth embodiment mentioned above.

As can be understood from the foregoing, according to the present invention, in addition to reducing the height of the diopter adjusting device, which is a significant technical advantage, the beams emitted from the light emitting optical system can be made incident upon the photographer's eye as a bundle of parallel beams even when a part of the lenses, which constitutes the view finder, is moved to adjust the diopter. The adjustment has minimal influence on the detection operation of the eye detector, resulting in a precise eye direction detection.

Figure 13:
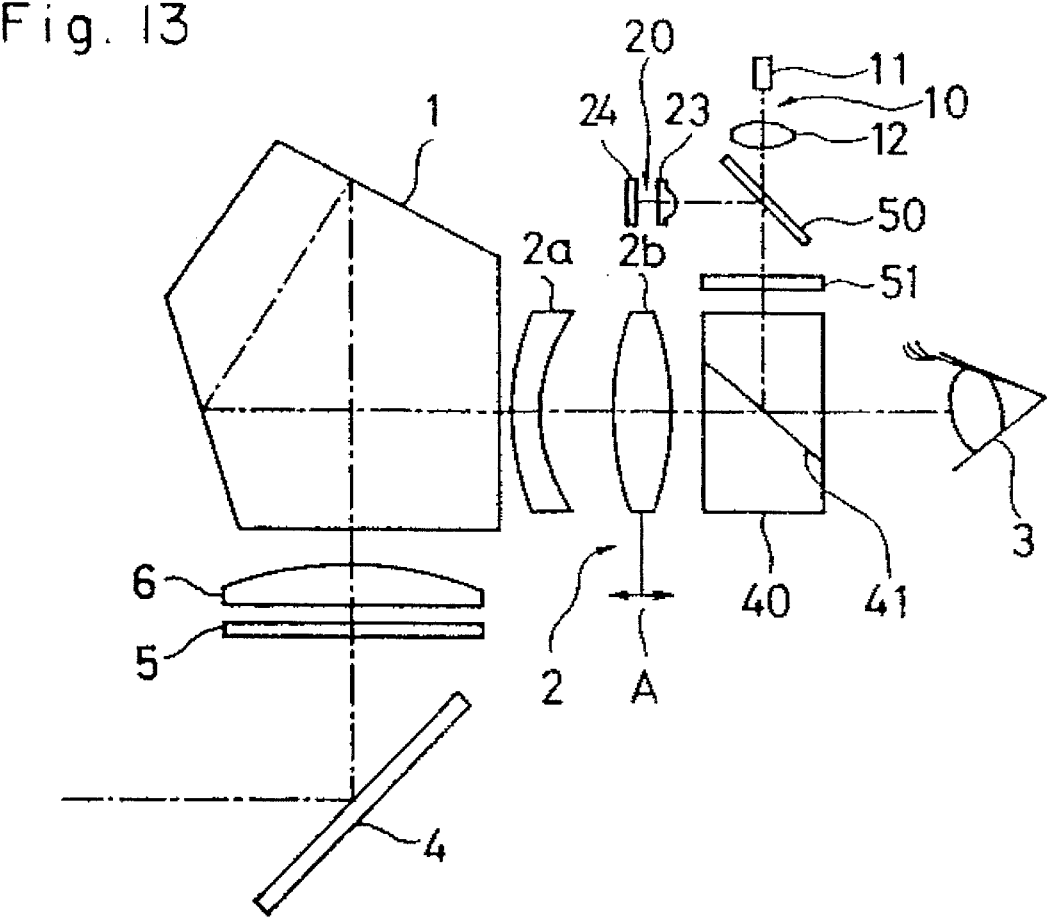
FIGS. 13 through 19 are side elevation views of a single lens reflex camera having an eye direction detecting device and a diopter adjusting device, according to different embodiments of the present invention.
Figure 14:
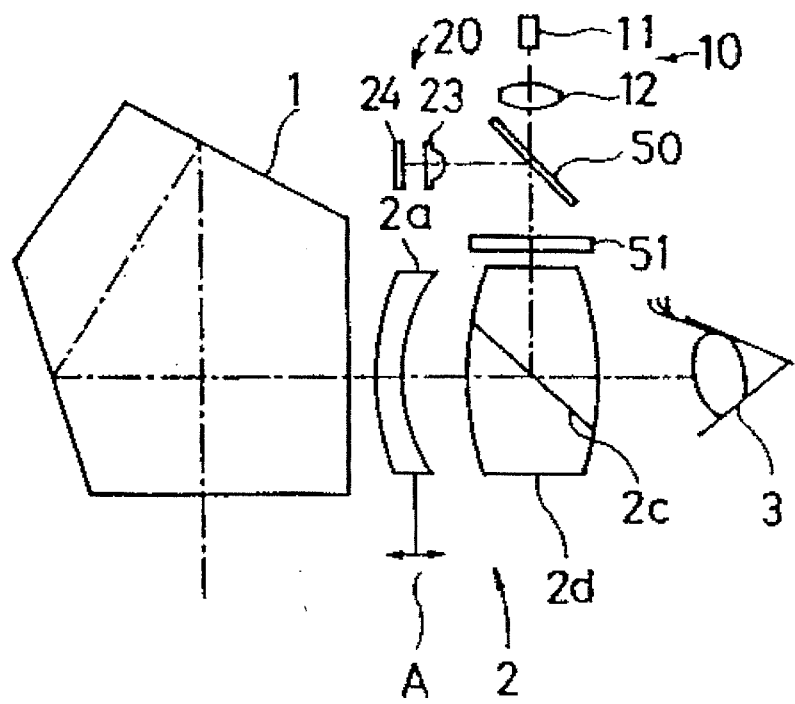
Figure 15:
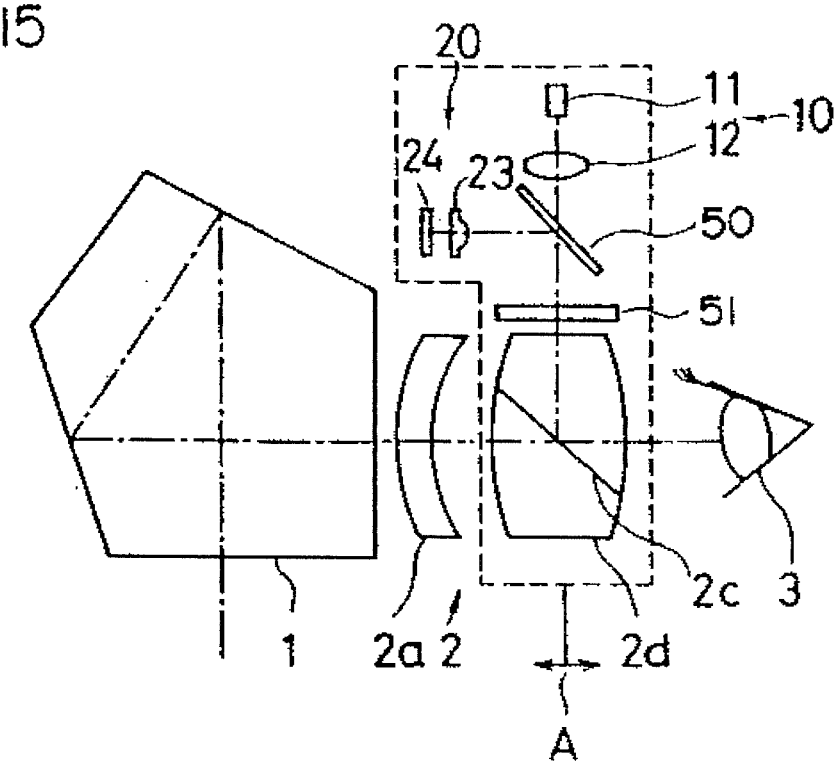
Figure 16:
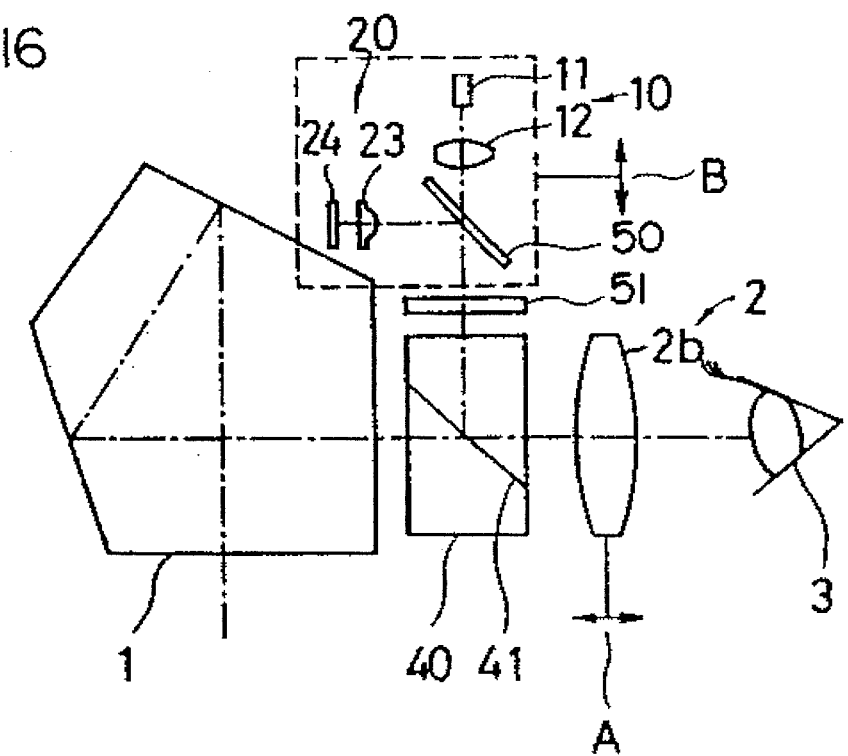
Figure 17:
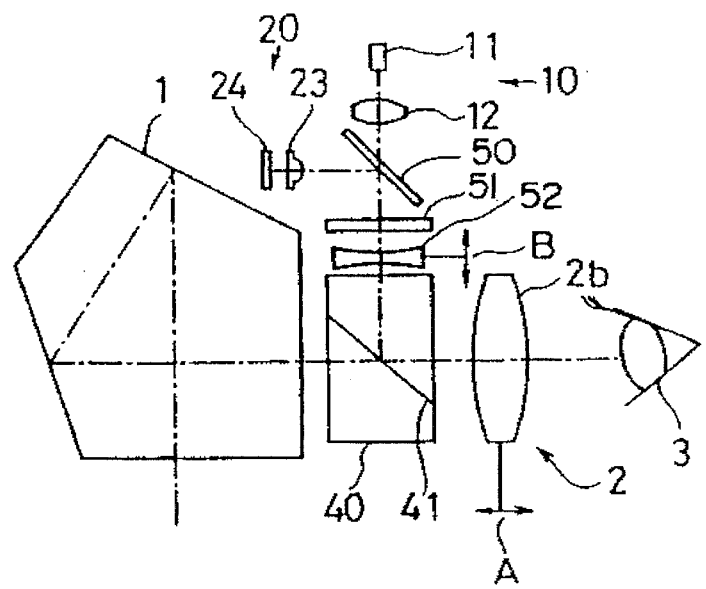
Figure 18:
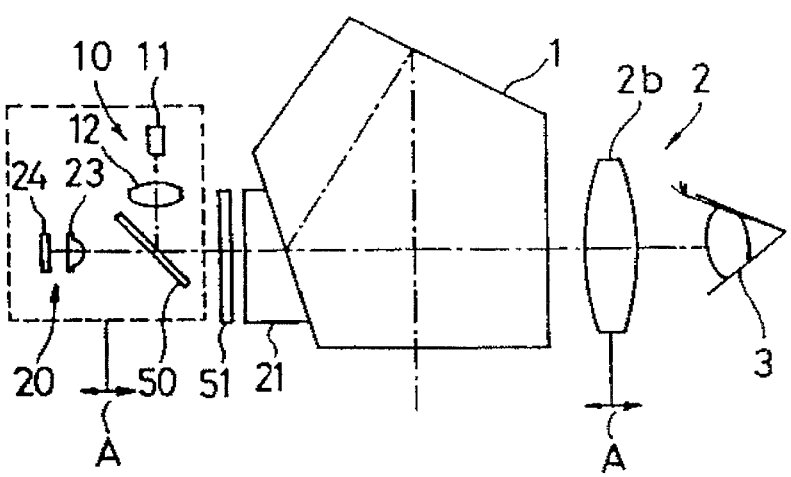
Figure 19:
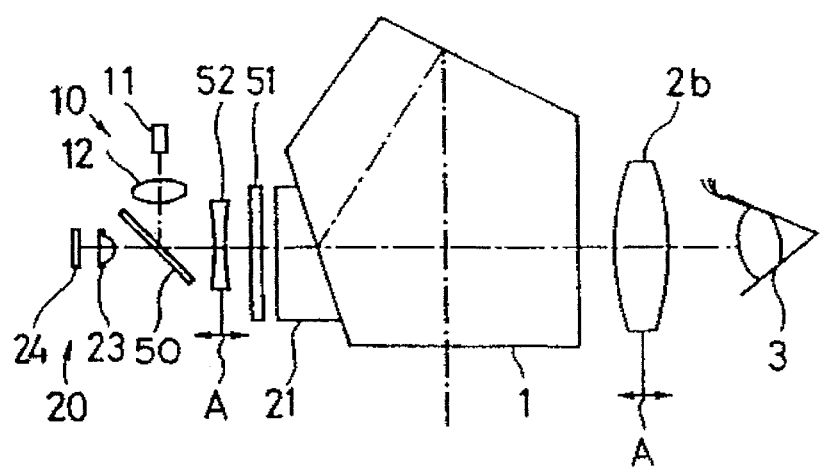

Other Embodiments:

FIGS. 13 and 19 show additional different embodiments of the present invention, in which the improvement is directed to the elimination of the influence on the eye direction detection upon the adjustment of the diopter adjusting device. Namely, these embodiments are not directed to decreasing the height of the eye detector.

In FIGS. 13 through 19, at least one of the optical axes of the light emitting and receiving optical systems 10 and 20 is located above the optical axis of the view finder in a normal posture of the camera. Namely, miniaturization of the eye detector in the vertical direction (i.e., vertical direction of the camera in a normal posture) is taken into account. Only the technical advantage concerning the elimination of the influence on eye direction detection upon an adjustment of the diopter is demonstrated in the embodiments shown in FIGS. 13 through 19.

FIGS. 13 through 19 correspond to FIGS. 6 through 12. In FIGS. 13 through 19, the elements corresponding to those in FIGS. 6 through 12 are designated with like reference numerals. The difference between FIGS. 13 through 19 and FIGS. 6 through 12 resides only in the direction of the optical axis of the light emitting optical system and/or the light receiving optical system. Consequently, it is apparent that the eye detection is not influenced by the adjustment of diopter in these embodiments.

Figure 20:
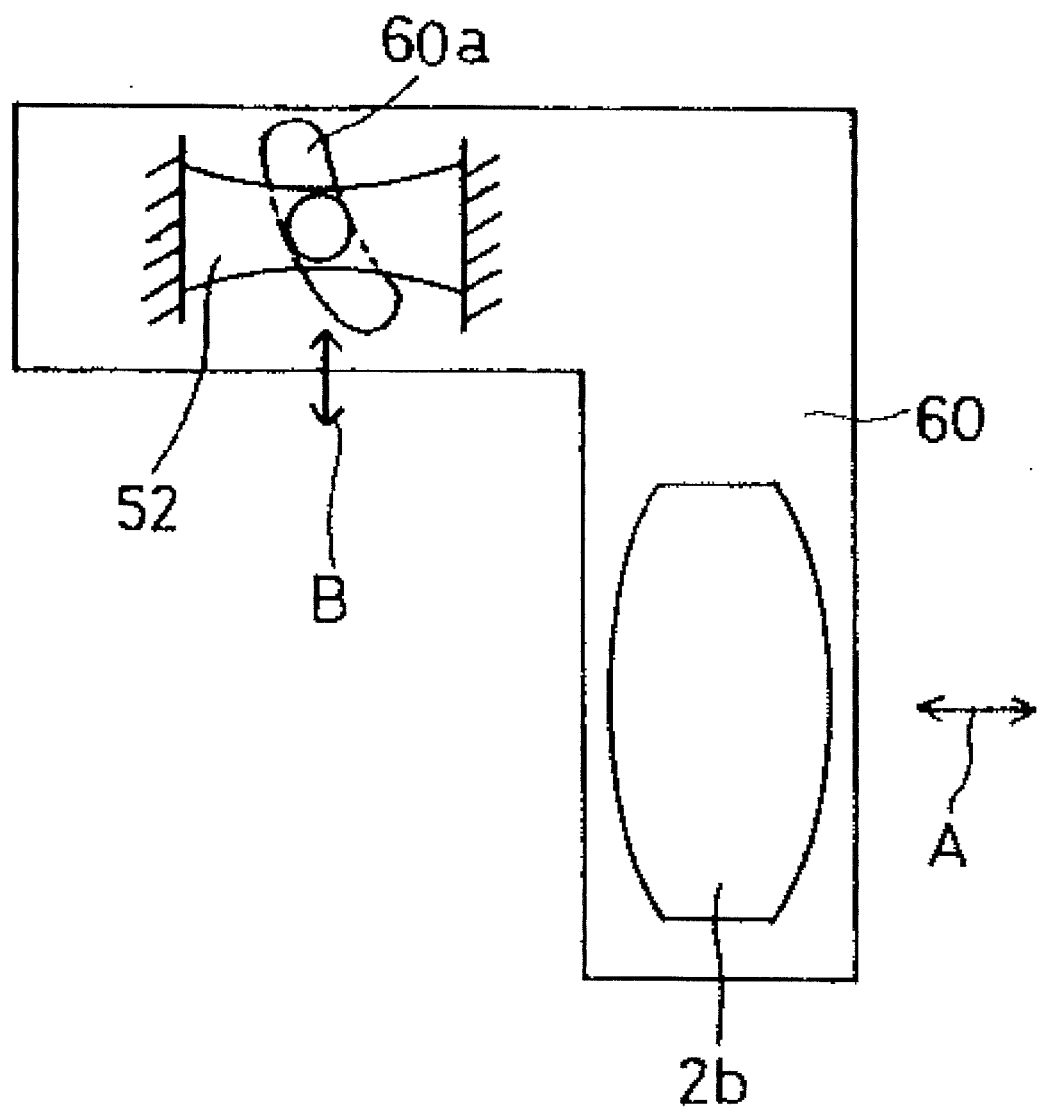
FIG. 20 is a side elevation view of a device for adjusting lenses to eliminate a negative influence of a diopter adjustment on the eye direction detecting device.

In FIG. 20, a cam mechanism is shown which is used to eliminate the influence on the eye direction detection upon the adjustment of the diopter. This type of device can be used for the eye direction detection apparatuses of FIGS. 9, 10, 16, and 17. When the positive lens 2b, which is in a fixed positional relationship with respect to cam plate 60 having a cam groove 60a, is moved to adjust the diopter in direction A, the adverse influence on the eye direction detection is eliminated by the corresponding movement of lens 52, which is guided to move linearly in direction B, with respect to cam groove 60a of cam 60.

I claim:

1. An eye direction detecting apparatus in association with a camera, in which a bundle of rays reflected from an object to be photographed is transmitted through a taking lens, reflected by a reflector, transmitted through an image erecting optical element and is made incident on a photographer's eye as an erect image, comprising:

a light emitting optical system which emits measuring light to be made incident upon said photographer's eye; and a light receiving optical system which receives light reflected from said photographer's eye to detect an eye direction, said light emitting optical system and said light receiving optical system being arranged so that optical axes of both said light emitting optical system and said light receiving optical system are positioned in a single plane normal to an optical axis of a bundle of rays incident upon said image erecting optical element through said taking lens.

2. An eye direction detecting device according to claim 1, further comprising an eyepiece lens which converges light, reflected from said object to be photographed, and transmitted through said taking lens, onto said photographer's eye.

3. The eye direction detecting apparatus of claim 1, wherein said optical axis adjacent said light emitting optical system and said optical axis adjacent said light receiving optical system are positioned in said single plane normal to said optical axis of said bundle of rays incident upon said image erecting optical element through said taking lens.

4. The eye direction detecting device of claim 1, wherein said optical axis of said light emitting optical system is located in a first plane and said optical axis of said light receiving optical system is located in a second plane, said first plane and said second plane comprising said single plane positioned in a plane normal to said optical axis of said bundle of rays incident upon said image erecting optical element through said taking lens.

5. The eye direction detecting apparatus of claim 1, wherein said optical axis of light emitted from said light emitting optical system and said optical axis of light incident upon said light receiving optical system are positioned in said single plane normal to said optical axis of said bundle of rays incident upon said image erecting optical element through said taking lens.

6. An eye direction detecting device in association with a camera, in which a bundle of rays reflected from an object to be photographed is transmitted through a taking lens and an image erecting optical element and is made incident on a photographer's eye as an erect image, comprising:

a light emitting optical system which emits measuring light to be made incident upon said photographer's eye;

a light receiving optical system which receives light reflected from said photographer's eye to detect an eye direction;

an eyepiece lens which converges light, reflected from said object to be photographed, and transmitted through said taking lens, onto said photographer's eye;

a diopter adjusting device for moving at least a part of said eyepiece lens in an optical axis direction, so that a direction of said measuring light upon said photographer's eye does not change upon adjustment of a diopter, wherein said light emitting optical system and said light receiving optical system are arranged so that optical axes thereof lie in a plane normal to an optical axis of a bundle of rays incident upon said image erecting optical element through said taking lens.

7. An eye direction detecting device according to claim 6, further comprising beam splitting means for separating optical paths of said light emitting optical system and said light receiving optical system from said optical path of light reflected from said object to be photographed.

8. An eye direction detecting device according to claim 7, wherein said eyepiece lens is located closer to said taking lens than to said beam splitting means.

9. An eye direction detecting device according to claim 7, wherein said beam splitting means is located closer to said taking lens than to at least a part of said eyepiece lens.

10. An eye direction detecting device according to claim 9, wherein at least a part of said eyepiece lens, said light emitting optical system, and said light receiving optical system are associated with each other through said diopter adjusting device.

11. An eye direction detecting device according to claim 9, further comprising a lens for adjusting said optical path of said light emitting optical system, said light receiving optical system being provided in said optical path of said light emitting optical system and said light receiving optical system.

12. An eye direction detecting device according to claim 11, wherein at least a part of said eyepiece lens and said adjusting lens are associated with each other through said diopter adjusting device.

13. An eye direction detecting device according to claim 3, wherein said light emitting optical system emits measuring light through a part of said view finder to be made incident upon said photographer's eye.

14. A camera, in which a bundle of rays reflected from an object to be photographed and transmitted through a taking lens is made incident on a photographer's eye through an eyepiece lens, comprising:

a light emitting optical system which emits measuring light to be made incident upon said photographer's eye;

a light receiving optical system which receives light reflected from said photographer's eye to detect a photographer's eye direction; and a diopter adjusting device which moves at least a part of said eyepiece lens in an optical axis direction, so that a direction of said measuring light upon said photographer's eye does not change upon adjustment of a diopter.

15. A camera according to claim 14, further comprising beam splitting means for separating optical paths of said light emitting optical system and said light receiving optical system from an optical path of light reflected from an object to be photographed.

16. A camera according to claim 15, wherein said eyepiece lens is located closer to said taking lens than to said beam splitting means.

17. A camera according to claim 15, wherein said beam splitting means is located closer to said taking lens than at least a part of said eyepiece lens.

18. A camera according to claim 17, wherein at least a part of said eyepiece lens, said light emitting optical system, and said light receiving optical system are associated with each other by said diopter adjusting device.

19. A camera according to claim 17, further comprising a lens for adjusting said optical path of said light emitting optical system, said light receiving optical system being provided in said optical path of said light emitting optical system and said light receiving optical system.

20. A camera according to claim 19, wherein at least a part of said eyepiece lens and said adjusting lens are associated with each other through said diopter adjusting device.

21. A camera according to claim 14, wherein said light emitting optical system emits measuring light to be made incident upon said photographer's eye through a part of said view finder.

22. A camera, in which a bundle of rays reflected from an object to be photographed and transmitted through a taking lens is made incident on a photographer's eye through an eyepiece lens, comprising:

a light emitting optical system which emits measuring light to be made incident upon said photographer's eye;

a light receiving optical system which receives light reflected from said photographer's eye to detect said photographer's eye direction; and means for adjusting a diopter so that a direction of said measuring light upon said photographer's eye does not change upon the adjustment of said diopter.

23. A camera according to claim 22, wherein said means for adjusting a diopter moves at least a part of said eyepiece lens in an optical axis direction.

24. A camera according to claim 22, wherein said light emitting optical system emits measuring light to be made incident upon said photographer's eye through a part of said view finder.

* * * * *

UNITED STATES PATENT AND TRADEMARK OFFICE
CERTIFICATE OF CORRECTION

PATENT NO. : 5,541,701
DATED : July 30, 1996
INVENTOR(S) : Takayuki SENSUI

It is certified that error appears in the above-indentified patent and that said Letters Patent is hereby corrected as shown below:

At column 8, line 48 (claim 13, line 2), change "3" to —6—.

Signed and Sealed this

Twenty-fifth Day of March, 1997

Attest:

BRUCE LEHMAN

Attesting Officer    Commissioner of Patents and Trademarks